United States Patent [19]
Luong et al.

[11] Patent Number: 5,411,866
[45] Date of Patent: May 2, 1995

[54] METHOD AND SYSTEM FOR DETERMINING BIOACTIVE SUBSTANCES

[75] Inventors: John H. T. Luong, Mount Royal; Keith B. Male, Pierrfonds; Maurice V. Cattaneo, Outremont, all of Canada

[73] Assignee: National Research Council of Canada, Ottawa, Canada

[21] Appl. No.: 39,998

[22] Filed: Mar. 30, 1993

[51] Int. Cl.$^6$ .................. C12Q 1/54; C12Q 1/26; C12Q 1/00; C12M 1/40
[52] U.S. Cl. .................. 435/14; 435/13; 435/15; 435/16; 435/4; 435/24; 435/25; 435/26; 435/288; 204/403
[58] Field of Search .......... 435/14, 13, 16, 24, 435/26, 4, 15, 288, 25; 204/403

[56] References Cited
U.S. PATENT DOCUMENTS

| | | | |
|---|---|---|---|
| 3,539,455 | 10/1975 | Clark | 435/16 |
| 4,299,669 | 11/1981 | Obana et al. | 435/288 |
| 4,376,689 | 3/1983 | Nakamura et al. | 435/288 |
| 4,384,936 | 5/1983 | Obana et al. | 435/25 |
| 4,614,714 | 9/1986 | Kusakabe et al. | 435/25 |
| 4,790,191 | 10/1988 | Romette et al. | 435/16 |
| 4,812,220 | 3/1989 | Iida et al. | 435/4 |

FOREIGN PATENT DOCUMENTS 2845820 4/1979 Germany.

OTHER PUBLICATIONS

Rosario et al, Analytical Chem., vol. 62, No. 22, (Nov. 15, 1990), pp. 2418–2424.
Hendry et al; Jour of Biotechnology, 15 (1990) 229–238.
Cattaneo et al; Biosensors & Bioelectronics 7 (1992) 329–324.
Clark, Leland C.; The Enzyme Electrode, Biosensors: Fundamentals & Applications, Turner, Karube & Wilson, eds., Oxford Science Publications, 1987, Oxford, pp. 1–12.
Chem. Abstract 118(25): 251031k (Male et al) 1992.

*Primary Examiner*—William H. Beisner
*Assistant Examiner*—Louise N. Leary
*Attorney, Agent, or Firm*—Juliusz Szereszewski

[57] ABSTRACT

An apparatus and method for measuring glutamine and glucose in certain cell cultures and body fluids in the presence of interfering endogenous compounds e.g. ascorbic acid, uric acid or glutamic acid. Prior to enzymatic degradation and amperometric detection of the products or elements resulting from the degradation, the interfering substances are retained by an anion exchanger disposed upstream of the enzymatic degradation site. The conditions of the method are controlled to utilize the difference of isoelectric points of the measured biosubstance and of the interfering compounds respectively.

7 Claims, 5 Drawing Sheets

METHOD AND SYSTEM FOR DETERMINING BIOACTIVE SUBSTANCES

FIELD OF THE INVENTION

This invention relates to an amperometric biosensor system and method for determining certain bioactive substances, or biosubstances, particularly glutamine in cell culture samples, for example during cell cultivation processes, and glucose in urine and blood samples. More particularly, the invention provides a method and apparatus for determining glutamine or glucose using enzymatic degradation and amperometric detection, in the presence of interfering compounds.

BACKGROUND OF THE INVENTION

Regulation of glutamine during mammalian or insect cell culture cultivation is of vital importance for optimization of cell growth and its productivity. Cell cultivation under depleted glutamine causes severe growth limitation, whereas increasing glutamine beyond a certain limit produces ammonia at toxic levels. Therefore it is critical to regulate glutamine during the course of cultivation processes. The determination of glutamine is also of importance in a clinical laboratory. Cerebrospinal glutamine levels are used with blood ammonia determinations in diagnosis of hepatic encephalopathy. Elevated glutamine levels are reported in parenteral nutrition, meningitis and in cerebral haemorrhage.

HPLC technique, commonly used for determination of glutamine, is time-consuming, expensive and requires skilled personnel.

U.S. Pat. No. 4,790,191 issued Oct. 25, 1988 to Romette et al. proposes an apparatus for measuring L-glutamine in a liquid sample. The apparatus includes a membrane on which are immobilized the enzymes glutaminase and glutamate oxidase. Glutamine in the sample is acted upon by the enzymes to form an enzymatic reaction product. The membrane is associated with a sensor, e.g. an oxygen electrode, which is capable of sensing either the product or a compound or element consumed or liberated in the process.

While the biosensor of the U.S. patent is useful, it has a drawback in that endogenous glutamic acid (also referred to in the literature as glutamate) present in the sample, i.e. cell culture medium, will interfere with the glutamine signal as the reaction of glutamine with glutaminase also yields glutamic acid. The sensor will therefore detect both glutamine and glutamic acid. In order to overcome this problem, a second measurement ("reference test") can be employed using immobilized glutamate oxidase alone as a reference analysis. This approach is both cumbersome and time-consuming since the membrane containing both immobilized glutamate oxidase and glutaminase (for determination of both glutamine and glutamic acid) and the membrane containing only immobilized glutamate oxidase (for determination of glutamate only) have to be interchanged during the course of measurement. In addition, this approach is only applicable for measurements in which the level of glutamine is significantly higher than that of glutamate (at least by the factor of ten). Further, oxygen based biosensors exhibit poor sensitivity due to their high current background (see Amperometric Biosensors, S. P. Hendry et al., Journal of Biotechnology, 15 (1990) 229-238). In this regard, hydrogen peroxide electrodes have been found superior to oxygen electrodes (Cattaneo et al., Monitoring Glutamine in Mammalian Cell Cultures Using an Amperometric Biosensor, Biosensors and Bioelectronics, 7 (1992) 329-334). However, endogenous glutamate interferes with the glutamine signal and a second measurement for the determination of glutamate is required.

It should be noted that a major disadvantage related to the use of hydrogen peroxide electrodes is the magnitude of the potential applied necessary for hydrogen peroxide measurement (+0.5 to +0.8 V, platinum vs. silver/silver chloride). Electroactive substances such as uric acid, ascorbic acid, acetaminophen etc. are known as potent interferents at this level. Such a drawback thus limits the widespread application of hydrogen-peroxide based biosensors for physiological samples or foodstuffs.

The determination of glucose levels in biological samples is an indispensable test for the diagnosis and therapy of certain illnesses, e.g. diabetes mellitus. The normal blood glucose level is about 90 mg/dL (5 mM) whereas the pathological value may increase up to 900 mg/dL (50 mM). Among several analytical procedures for the determination of glucose, electrochemical detection of enzymatically generated hydrogen peroxide is probably the most developed type of glucose biosensor. Amperometric glucose biosensors using immobilized glucose oxidase together with a sensitive hydrogen peroxide electrode have been used for in vitro and in vivo monitoring because of the high specificity of this enzyme for $\beta$-D-glucose (Keilin et al., Biochem. J. 50, 1952, 331). In such a biosensor, the enzyme glucose oxidase catalyzes the oxidation of glucose to D-glucono-$\delta$-lactone and hydrogen peroxide. The latter then contacts with a platinum anode vs silver/silver chloride cathode poised at +0.7 V where electrochemical oxidation takes place, and the current generated is directly proportional to the glucose concentration in the measured sample. Unfortunately, hydrogen peroxide amperometric detection is also sensitive to several naturally occurring electron donors, such as ascorbate, urate, acetaminophen, and so forth. Blood and urine contain significant concentrations of urate and ascorbate.

Among several methods proposed to improve the selectivity of the glucose biosensor against such electrochemically interfering substances, one solution is to form a differential system i.e to compensate the response by the addition of a second electrode not associated with glucose oxidase, see Clark, L. C., Biosensors: Fundamentals and Applications, Turner, Karube and Wilson, eds, Oxford Science Publications, 1987, Oxford, pp. 1-12. Another approach is described in U.S. Pat. No. 3,539,455 to Clark. It uses a permselective membrane (e.g. cellulose acetate) to cover the platinum anode. This type of membrane only allows the diffusion of small molecules such as oxygen or hydrogen peroxide, but excludes ascorbate and other large-particle potential interfering substances. The main disadvantage of this approach is that it creates an additional diffusion layer that adversely affects the sensitivity and the response of the enzyme electrode.

SUMMARY OF THE INVENTION

It is an object of the present invention to simplify the determination of glutamine or glucose in liquid samples of the type described hereinabove.

It is another object of the present invention to reduce the interference of certain substances during the determination of glutamine using the bi-enzyme approach.

It is still another object of the invention to reduce the electroactive interference of certain substances during the determination of glucose in blood and urine samples using the glucose oxidase.

According to the invention, there is provided an apparatus, or system, for measuring a biosubstance in a liquid sample using enzymatic oxidation of the substance and amperometric detection of the resulting product or element, in the presence of compounds interfering with the measurement, the apparatus comprising:

an ion exchange means capable of at least partly removing from the sample passed therethrough the interfering substances while leaving the measured biosubstance in the sample, immobilized enzyme means suitable for the degradation of the measured biosubstance, the enzyme means associated with the ion exchange means downstream thereof, and a sensor capable of sensing a product or element resulting from the enzymatic degradation of said biosubstance to produce a signal indicative of the concentration of the biosubstance in the sample.

The immobilized enzyme means is selected to include an oxidase corresponding to a given biosubstance. For determination of glutamine, the enzymes can be glutaminase and glutamate oxidase; for glucose, glucose oxidase can be used.

Preferably, the ion exchange means is an anion exchange means capable of retaining at least one compound from the group consisting of glutamic acid, aspartic acid, acetaminophen, ascorbic acid and uric acid, and their salts.

Preferably, the sensor is a hydrogen peroxide sensor but an oxygen sensor (e.g. an oxygen electrode) can also be used as known in the prior art.

In another aspect of the invention, there is provided a method of measuring a biosubstance selected from glutamine and glucose in a liquid sample using enzymatic oxidation of the biosubstance and amperometric detection of a product or element resulting from the degradation, the sample also comprising substances interfering with the measurement, the method comprising a) passing said sample through an ion exchange means at a pH selected to impart a different electric charge on the particles of the interfering substances in said sample compared to the electric charge on the particles of the biosubstance, thereby to effect at least a partial retention of said interfering substances by the ion exchange means, then b) subjecting said sample to enzymatic degradation to form an enzymatic reaction product, and c) sensing the concentration of said product or another compound or element consumed or liberated in the formation or degradation of said product, said concentration being indicative of the concentration of the biosubstance in the sample.

The separating step a) is carried out at conditions suitable for at least partly retaining the interfering substances while allowing the measured biosubstance to pass through the ion exchange means.

Preferably, the ion exchange means is an anion exchange resin.

The pH of the sample in step a) is above the highest isoelectric point of the interfering substances and below the isoelectric point of the measured biosubstance.

BRIEF DESCRIPTION OF THE DRAWINGS

In the drawings which illustrate the invention in more detail.

DETAILED DESCRIPTION OF THE PREFERRED EMBODIMENTS

Figure 1:
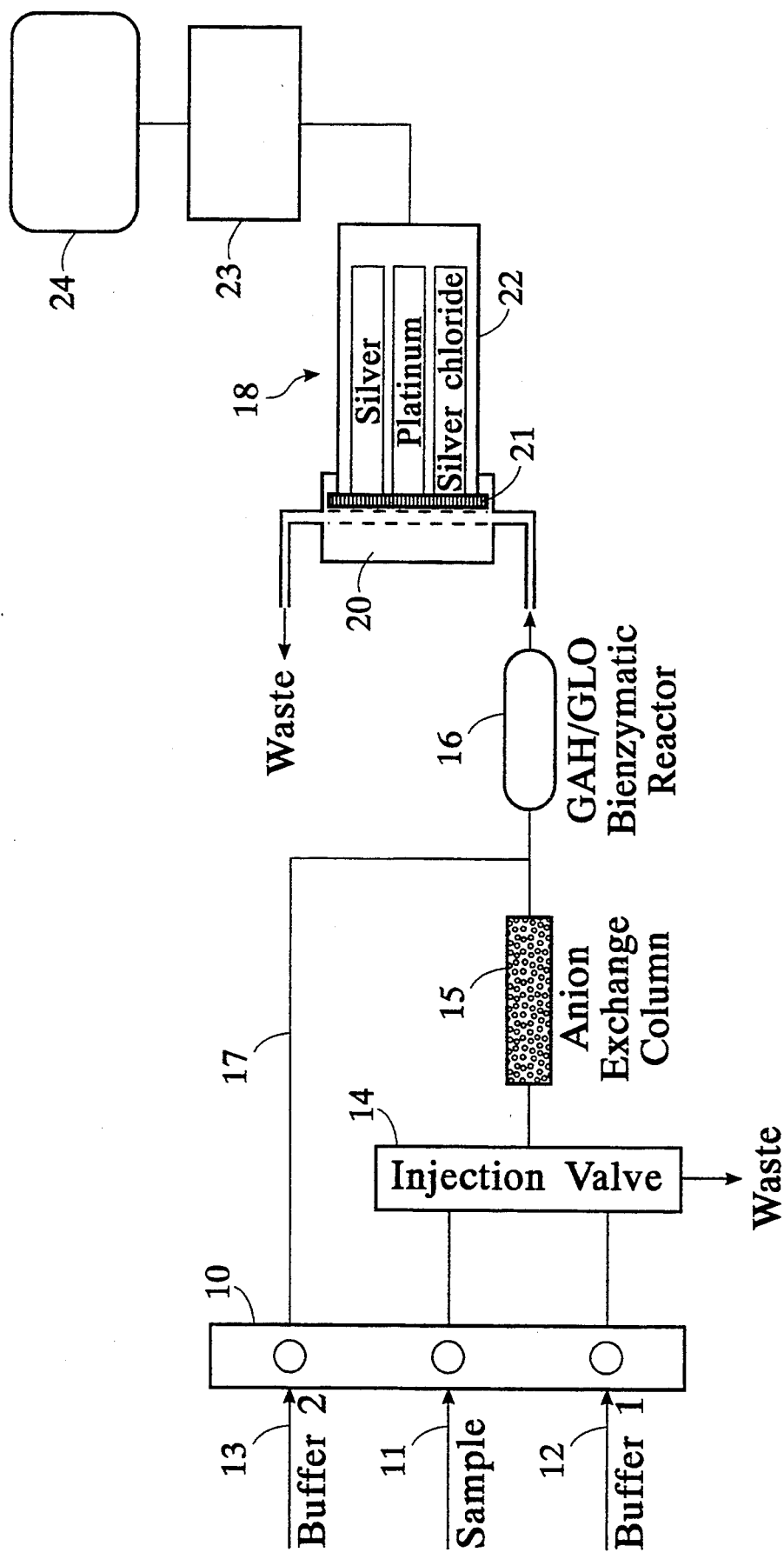
FIG. 1 is a schematic diagram of an embodiment of the apparatus of the invention.

While the invention was validated by testing glutamine and glucose only, it can be reasonably concluded that the scope of the invention can be extended to other, untested biosubstances and corresponding oxidases.

Glutamine Determination

For the determination of glutamine, similarly as the prior art method of U.S. Pat. No. 4,780,191, the present invention uses the bi-enzyme approach i.e. the coupled reactions of glutaminase and glutamate oxidase with glutamine. The reactions can be illustrated as follows:

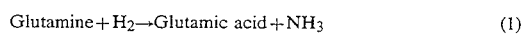
$$\text{Glutamine} + H_2 \rightarrow \text{Glutamic acid} + NH_3 \tag{1}$$

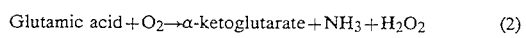
$$\text{Glutamic acid} + O_2 \rightarrow \alpha\text{-ketoglutarate} + NH_3 + H_2O_2 \tag{2}$$

Glutamic acid is an amino acid with two carboxyl groups and one amino group. It has an isoelectric point of 3.22. The isoelectric point of glutamine is 5.65. Therefore, a selected ion exchange means, for example an anion exchange resin should separate glutamic acid or its sodium salt from glutamine by retaining glutamate particles which possess a net negative charge and not retaining neutral or positively charged glutamine particles.

Materials

Glutamate, glutaraldehyde (25% w/v), glutaminase (GAH, EC.3.5.1.2) and porous aminopropyl glass beads were purchased from Sigma (St. Louis, Mo.). L-glutamate oxidase (GLO) was purchased from Yamasa Shoyu Ltd. (Choshi, Chiba, Japan). Anion exchange resins AG1-X8 were obtained from Bio-Rad Laboratories (Richmond, Calif.). A glutamine standard (200 mM) for cell culture was supplied by Gibco Laboratories (Grand Island, N.Y.). Immunodyne TM activated membrane (3 μm pore size) was purchased from Pall Biosupport Corporation (Glencove, N.Y.).

Immobilization of the enzymes on aminopropyl glass beads.

Two batches (250 mg) of aminopropyl glass beads (80-120 mesh, 70 nm pore size) were washed extensively with phosphate buffer saline, PBS (9 g/liter sodium chloride, 20 mM phosphate, pH 7) and then activated by contacting with 3 ml of 2.5% (w/v) glutaraldehyde in PBS for 2-3 h at room temperature (20°-24° C.). The resulting orangish-pink beads were washed thoroughly with PBS pH 5.3 followed by 20 mM phosphate pH 5.3 to remove excess glutaraldehyde.

A 3 ml solution of glutaminase (16.7 U/ml and 96 U/mg protein) or glutamate oxidase (8.3 U/ml and 27 U/mg protein) in 20 mM phosphate buffer pH 5.3 was then covalently immobilized to each batch of activated beads and rotated end-over-end in a capped test tube overnight at 4° C. In both cases, experimental results confirmed that there was no evidence of any enzyme activity or protein content in the supernatants. After immobilization, the beads were mixed together and packed into a piece of tygon tubing (2.54 mm ID, 8 cm in length), furnished with glasswool at the ends to retain the beads (0.5 g of beads will pack into approximately 3 columns). The GAH/GLO column was stored in 50 mM acetate/100 mM NaCl buffer pH 5.3 at 4° C. Optimum operating conditions for glutamine conversion were determined with respect to buffer type and strength, pH, NaCl concentration, enzyme column length and flow rate.

Anion Exchange Resins

Anion exchange resins were tested to validate the invention. They were obtained from Bio-Rad Laboratories (Richmond, Calif.). Three forms of resins—hydroxyl, acetate and chloride were analyzed at three different particle sizes: 20-50 mesh (1190-420 $\mu$m), 100-200 mesh (180-106 $\mu$m), and 200-400 mesh (106-45 $\mu$m). The best results were obtained with acetate resins (AG 1-X8 TM or Aminex anion resins, analytical grade) having the active group $R-CH_2N^+(CH_3)_3$.

The resins were packed into a 2.54 mm ID piece of tygon tubing of 12 cm in length, furnished with glasswool at the ends to retain the resins. Optimum conditions for glutamate adsorption were determined with respect to flow rate, pH and buffer concentration. Optimum conditions for adsorption of uric acid, ascorbic acid and acetaminophen by the resins were also studied. To construct equilibrium isotherms for identifying the selectivity characteristics of the resin for ascorbic acid, uric acid and acetaminophen with respect to acetate, 15 ml solutions of differing compound/acetate fractions were equilibrated with batches of resins. The total concentration was 100 mM, 50 mM and 1 mM while the amount of dry resin (estimated as 50% wet resin) used was 0.5 g, 0.25 g and 0.010 g for ascorbic acid, acetaminophen and uric acid, respectively. For each compound, equilibrium was obtained within 30 min and the concentrations in the liquid fractions were measured spectrophotometrically (compared to time 0 min) at 245 nm, 240 nm, and 290 nm for ascorbic acid, acetaminophen and uric acid, respectively. The selectivity coefficient was calculated for the compounds at different pH and temperature operating conditions.

Apparatus

Referring now to FIG. 1, the apparatus of the invention is embodied by a flow injection analysis (FIA) system which consists of a peristaltic pump 10 to which are connected a sample line 11, a buffer 1 line 12 and a buffer 2 line 13. The peristaltic pump 10 is connected with a motorized injection valve 14. An anion exchange column 15 is disposed downstream of the injection valve 14, the column also being connected to a bi-enzymatic reactor 16. A line 17 supplies buffer 2 from the peristaltic pump 10 to the line connecting the column 15 with the reactor 16. The latter is connected to a detecting module 18 which includes a temperature controlled flow cell 20 and an amperometric hydrogen peroxide electrode 22 (platinum vs. silver/silver chloride at +0.7 V). An Immunodyne TM membrane 21 (Pall Biosupport Corporation, Glencove, N.Y., USA) is tightly attached to the electrode and held in place by an O-ring (not shown) to alleviate the interference caused by the liquid flow pattern around the electrode. The sampling and injection into the system is controlled by a master module (Eppendorf North America Inc., Madison, Wis.), not illustrated. The master module also performed data acquisition in peak height or peak area mode. The output signal of the amperometric electrode 22 after conversion of the current signal to voltage by potentiostat 23 is recorded on a strip chart recorder 24. In peak height mode, the response was expressed as relative units (RU) in which 1 RU is equal to 2.86 $\mu$V at the detection output.

Measurement of Glutamine Concentration

The anion exchange column was placed in the sample flow line before the GLO/GAH column in order to remove endogenous glutamate (glutamic acid), as shown in FIG. 1. The glutamine standard for cell culture was diluted in 1 mM acetate buffer pH 5.3 for preparation of standard curves. Cell culture supernatants were diluted ten- to thirty-fold in the above buffer.

The insect cell culture samples were taken from culture supernatants of *Spodoptera frugiperda*, Sf-9 (fall armyworm), producing recombinant proteins. Using a bioreactor (3.5-11 L), Sf-9 cultures were grown in Grace's insect cell medium (Gibco, Grand Island, N.Y.), supplemented with 10% (v/v) fetal bovine serum (Hyclone, Logan, Utah), 3.3 g/l TC yeastolase (Difco, St. Louis, Mo.), 3.3 g/l TC lactalbumin hydrolysate (Difco) and 0.1% (w/v) pluronic F-68 (JRH Biosciences, Lenexa, Kans.). The initial concentration of both glutamine and glutamic acid in the Grace's medium was 4.1 mM. However, in certain experiments the initial glutamine concentration was elevated three-fold.

The mammalian cell culture samples were taken from culture supernatants of murine hybridoma cells producing monoclonal antibodies against blood cell antigens. The cells were cultured in a 1.5 liter Celligen bioreactor (New Brunswick Sci., Edison, N.J.) using a protein free medium containing 1.9 mM glutamine and 1 mM glutamate (PFHM media, Gibco, Grand Island, N.Y.) further augmented to 3.9 mM glutamine. At various stages of either culture system, the samples were withdrawn aseptically and the cells were separated from the culture media by centrifugation. The resulting supernatants were stored at $-80°$ C. until further use.

The samples were analyzed for glutamine by the present FIA system as well as by standard HPLC for comparison. The reversed phase HPLC method was adapted from S. S. Seaver, Commercial Production of Monoclonal Antibodies, Marcel Dekker, New York 1987, pp. 315-317; the protocol was highly specific for glutamine. Samples were diluted six-fold with an aqueous homoserine solution (0.28 g/l) which was used as an internal standard. A volume of 50 $\mu$l of these diluted samples was mixed with 100 $\mu$l of orthophthalaldehyde (Fluoroaldehyde, Pierce Chemical Co., Ill.) and the resulting mixture was injected in the HPLC system (Waters, model 715 Ultra Wisp, Mass.). The system was equipped with a RP8 Spheri 5 (25×0.46 cm, 5 μm column, Brown Lee Labs, Santa Clara, Calif.) maintained at 40° C. and a fluorescence detector (Waters, model 420 AC) with a 334 nm excitation filter and a 425 nm emission filter. The mobile phase was a mixture of methanol (A) and 1% tetrahydrofuran in a 0.05M $NaH_2PO_4$ aqueous solution, pH 7 (B). At 1.4 ml/min, the separation was achieved using a constant phase composition of 25% A and 75% B (v/v) for 6 minutes followed by linear gradients of both solvents for 24 minutes up to a final mixture composition of 65% A and 35% B. The reproducibility of the HPLC method for 5 repeated analyses at 95% confidence level was determined to be ±3%.

Optimization of Immobilized Enzyme System

Figure 2:
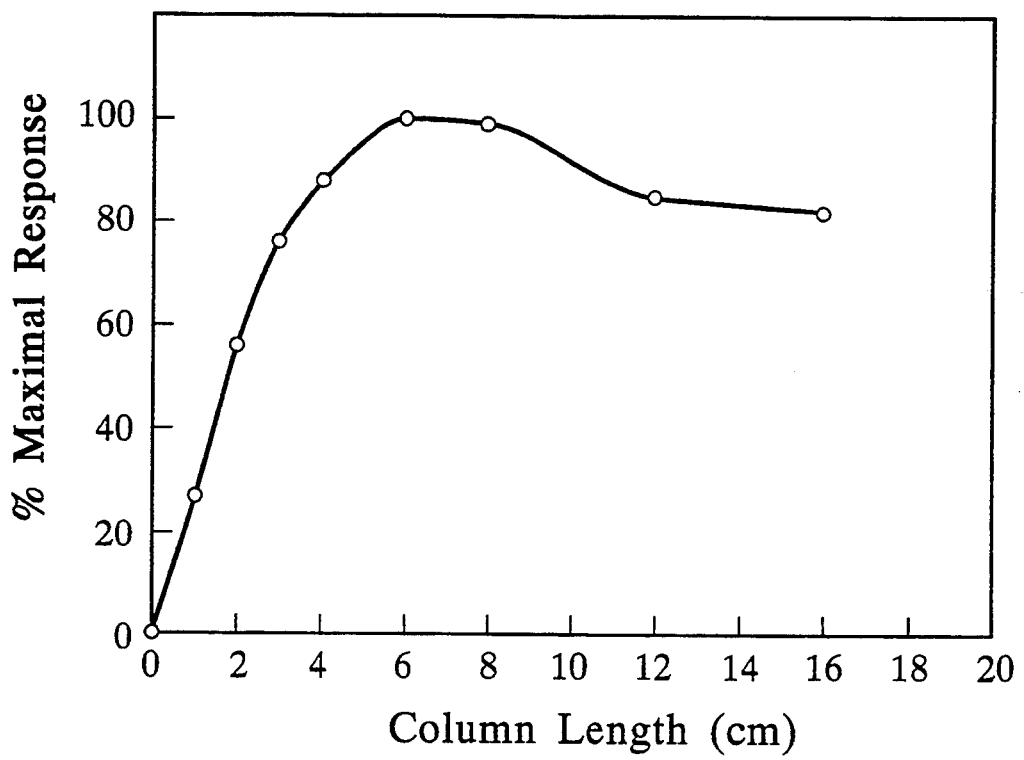
FIG. 2 is a graph illustrating the relationship between the enzyme column length and the response of a glutamine sensor to a 1 mM glutamine solution.

The GLO/GAH column was monitored with 1 mM glutamine using the configuration shown in FIG. 1 without the anion resin in place in order to establish optimal operating conditions. At the preset flow rate of 31 ml/h, a column length of 6-8 cm resulted in a maximal response (FIG. 2). An increase of the column length beyond 8 cm resulted in a decrease of the signal which could be due to the decomposition of the hydrogen peroxide produced along the column length. In FIG. 2, the relationship between the enzyme column length and the system response to 1 mM glutamine (in 1 mM acetate, pH 5.3) is illustrated at a flow rate of 31 ml/h with 100 mM acetate, 200 mM NaCl pH 5.3 buffer. As a compromise between the response and the reusability of the immobilized enzyme column, the 8 cm column length was then chosen for all subsequent optimization studies. This series of experiments was performed in peak area to account for the difference in peak heights caused by changing dispersions due to varying column lengths.

Similar responses were obtained for the four buffers tested at pH 5.3—citrate, acetate, phosphate and imidazole. However, acetate was chosen because of its increased buffering capacity over the desired pH range. The immobilized enzyme system responded maximally to glutamine in the pH range 4.4–5.6. Above pH 5.6 the response decreased rapidly with only 10% of the signal remaining at pH 5.9. However, the system was not inactivated since the normal response could be restored by lowering the pH. Such behavior was not completely unexpected since the optimal pH for native glutamate oxidase and glutaminase was 7 and 5.3, respectively and immobilized glutamate oxidase exhibited a broad optimum range (pH 5-9) whereas the activity of immobilized glutaminase dropped rapidly at pH above 5.5.

Although the maximal response was obtained from 25 mM to 100 mM acetate, the upper level was used for maintaining the pH of the buffer stream after mixing with cell culture samples. Increasing the acetate concentration beyond 100 mM adversely affected the system response since only 75% and 50% of the maximal response was detected at 200 mM and 500 mM, respectively. Addition of sodium chloride to the buffer was necessary to prevent fouling of both the immobilized enzyme column and the electrode surface. A concentration of 200 mM was chosen, since the response was only 70% and 45% of the maximal response at 500 mM and 1000 mM NaCl, respectively.

Figure 3:
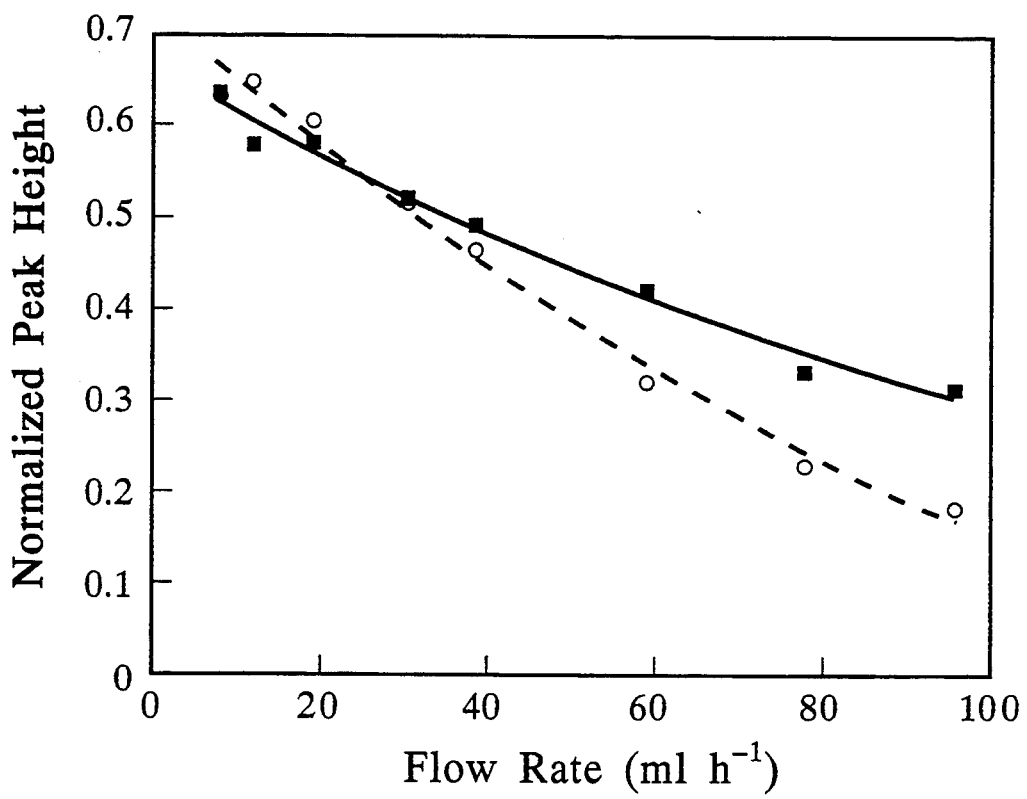
FIG. 3 illustrates the effect of flow rate on the response of the sensor at 75 μL injection volume.

FIG. 3 illustrates the effect of flow rate on the response of the system (normalized peak height) with 75 μl injection volume for both glutamate (■) and glutamine (○). Peak height was normalized with respect to the steady-state responses for a flow rate of 12 ml/h. The response increased with a decrease in the sample flow rate as expected in accordance with the theoretical prediction for FIA systems with negligible mass transfer resistance in the bulk solution, as well as experimental observations. As a compromise between sensitivity of analysis and sample throughput (assays per hour) a flow rate of 31 ml/h was selected for all subsequent studies. It should be noted that the total flow rate through the immobilized enzyme column will be 62 ml/h after the two streams merge. At this speed, the peak height response to glutamine is the same as that of glutamate (glutamic acid), whereas at higher speeds the retention time is not sufficient to achieve the same conversion rates for the two amino acids.

The above-mentioned anion exchange resin AG 1-X8 containing quaternary ammonium functional groups is capable of exchanging anions and possesses the following order of selectivity: Cl>acetate>OH. Columns containing the three above resin forms were monitored using the configuration of FIG. 1. Obviously, if anion exchange resin AG 1-X8 effectively retains glutamate, the injection of this amino acid to the present biosensor apparatus should provoke minimal or no response. However, the response to glutamine of the biosensor with or without the anion exchange column should be somewhat identical since such ion exchange resins are not anticipated to retain this amino acid.

To select the most suitable type of resin, a series of experiments was performed using a very large particle size resin, 20-50 mesh in order that effects would be more pronounced. Among the three different types of resins tested (chloride, acetate, and hydroxyl), the response to glutamate (1 mM) was 10%, 0.8% and 0.02%, respectively when compared with the signal obtained without the ion exchange column. Obviously, both acetate and hydroxyl resins retained glutamate much more efficiently that the chloride form. Further experimental data at pH 5.3 revealed that the use of hydroxyl resins also completely suppressed the glutamate signal while the acetate form did not affect the response of the present biosensor system to glutamine. Such behavior was also observed with the smaller particle size hydroxyl and acetate resins (100-200 mesh). Consequently, acetate resin was used in all subsequent studies to establish optimal operating conditions for the removal of glutamate.

The acetate buffer concentration used in the sample stream greatly affected the binding capability of the acetate resin (20-50 mesh) for glutamate. At low concentrations of acetate (<5 mM) only 1% of the glutamate passed through was detected by the biosensor of the invention. However, 10% and 30% of the glutamate were detected when the acetate concentration increased to 50 mM and 100 mM. Furthermore, the signals did not return to the normal zero baseline during the washing step implying a slow dissociation of bound glutamate from the resin. As expected, the sample stream flow rate also affected the glutamate binding capacity of the acetate resin column. Below 40 ml/h less than 1% of the injection of glutamate passed through the resin, whereas at 100 ml/h this value increased up to 5%.

For the system to be practical, the acetate (or generally, ion exchange) resin must be effective for an extended period of time, i.e. the column must possess a high binding capacity to glutamate and adsorbed glutamate must not be dissociated during the course of repeated measurements. In view of this, the binding capacity of the two smaller particle sizes (higher binding surface area) of acetate resins, 100–200 mesh and 200–400 mesh were evaluated by repeated injections of very high glutamate concentrations, 50 mM and 200 mM (in 1 mM acetate), respectively. Glutamate began to pass through after 10 injections as detected by the biosensor with the 100–200 mesh resin and after only 6 injections with the 200–400 mesh. Based on this result, the maximum binding capacity of 100–200 and 200–400 mesh resins was estimated to be 7 and 17 mg of glutamate, respectively. For a given volume of the column, decreasing the particle size will increase the overall surface area for binding and in turn will result in an increased glutamate binding efficiency.

Figure 4:
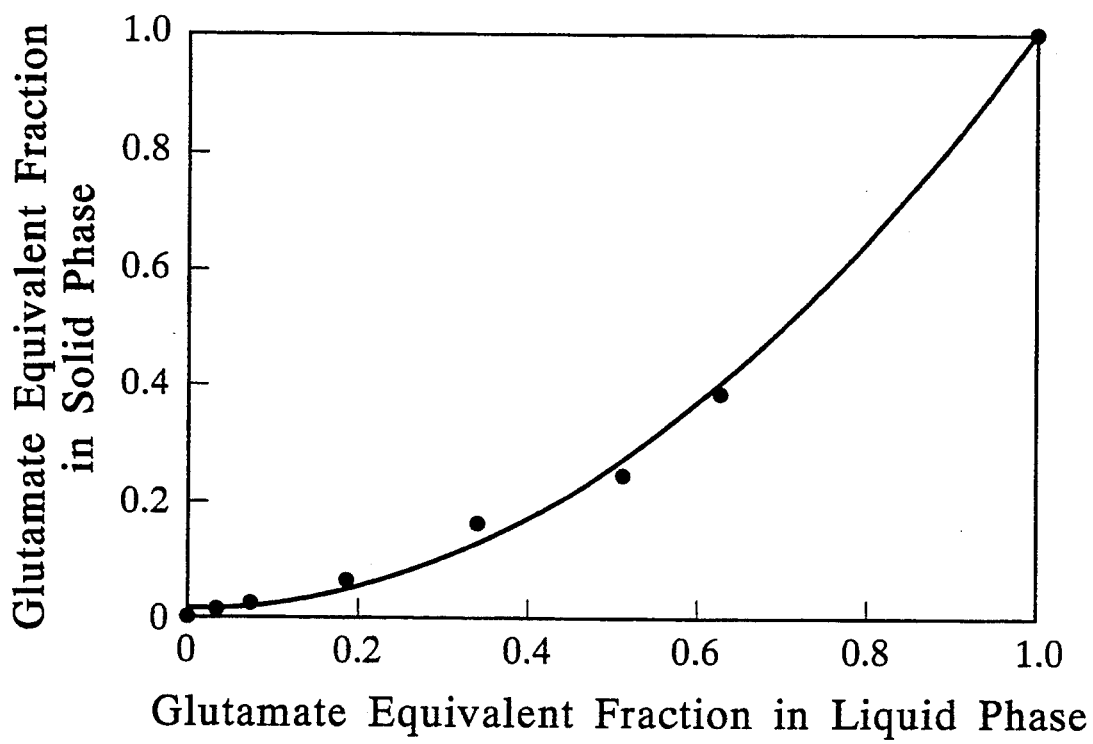
FIG. 4 illustrates an ion exchange isotherm of glutamate versus acetate.

For repeated injections of low glutamate concentration (1 mM), a condition which is somewhat close to the real application, the 100–200 mesh acetate resin lasted for 12 h (corresponding to about 3 mg of glutamate binding and 200 repeated analyses) before the glutamate signal was noticed. In order to construct an equilibrium isotherm for identifying the selectivity characteristic of the resin, 0.5 batches of the resin in the acetate form were equilibrated with 15 ml solutions of differing glutamate/acetate fractions. In this respect, FIG. 4 illustrates an ion exchange isotherm of glutamate versus acetate, with samples equilibrated at 21° C. and the total glutamate plus acetate concentration being equal to 0.1N. The glutamate equivalent fraction is defined as the glutamate concentration over the total acetate plus glutamate concentration. As shown in FIG. 4, the ion exchange isotherm displays a downward inflection, thus indicating a selectivity preference for acetate compared to glutamate. The selectivity coefficient was then estimated to be 0.4. The lower selectivity for glutamate hinted why a lower number of injections before breakthrough were obtained with the higher acetate buffer concentration. Evidently, higher acetate concentrations overload the resin with the preferred acetate ion and oppose the glutamate binding process. The isotherm also indicated low glutamate capacities (0.1 to 0.3 mmole/g) from this ion exchanger which is far from the theoretical 2.9 meq/s as reported by the manufacturer. In practice, real samples may contain a certain amount of other ions with higher selectivities than glutamate or acetate, e.g. chloride, which would tend to reduce the equilibrium capacity far below what was predicted from the isotherm.

Optimal Conditions of the System With Acetate Resin Column

The binding capacity of the acetate resin (100–200 mesh) column as a function of the acetate buffer concentration used in the sample line was reconfirmed. Under continuous injections of 1 mM glutamate, at high acetate concentrations (50 to 100 mM) the ion exchange column was only good for a single injection. However, at 5, 10 and 20 mM acetate concentrations the ion exchange column could be reused for 30, 10 and 5 repeated injections before glutamate was detected by the biosensor system. As a result of this finding, 1 mM acetate was chosen as the optimal running condition since the ion exchange column was anticipated to last for about 200 repeated injections of 1 mM glutamate.

The pH of the sample in the range of 5–7 did not have any noticeable effect on the binding efficiency of the glutamate. Such behavior should be anticipated since glutamic acid assumes net negative charge at pH above 3.22 as mentioned previously. Based on this finding and the isoelectric pH of glutamine (5.65), pH 5.3 (optimum for these immobilized enzymes) was chosen for the acetate buffer. It should be noted that when real samples were diluted in the sample buffer the pH remained in the range 6–7 due to the buffer strength of the sample. Unlike for the 20–50 mesh resin, samples containing glutamate passed through the 200–400 mesh acetate resin at flow rates up to 80 ml/h without being detected. Therefore by decreasing the particle size the residence time is no longer critical and the selected speed of 31 ml/h was considered compatible with the GAH/GLO column.

Similar results were also obtained for the flow rate (FIG. 3) when the ion exchange column was inserted into the system, except that the maximum normalized peak height was slightly lower (0.56 vs. 0.63).

Such behavior could be due to the introduction of the ion exchange column which induced more convection/diffusion dispersion in the flowing stream, thereby lowering the peak height response. This phenomenon was reported for the aspartame biosensor system (K. B. Male et al., Biosensors & Bioelectronics 1991, 6, 117–123) as well.

In peak height mode, there was an excellent linear relationship between the response of the system of the invention and glutamine up to 1 mM (correlation coefficient of 0.999). The sensitivity of the biosensor was determined to be $142 \pm 2.9$ RU/$\mu$M (95% confidence interval, n=9) with a minimum detectable level of 10 $\mu$M. A good reproducibility ($\pm 1.2\%$) was also obtained as reflected by the average response for 10 repeated analyses of 1 mM glutamine ($136,600 \pm 1589$ RU at 96% confidence interval). Each assay could be performed in 3.5 min. including washing, giving a throughput of 17 $h^{-1}$. Similarly, the response was also linear using peak area mode and the determination for glutamine in cell culture samples was identical in either peak area or peak height mode. However, the minimum detection level was considerably higher (50 $\mu$M). It should be noted that in peak area mode one has to define the threshold level for the baseline and for the peak detection, respectively. Therefore, it is somewhat more problematical to accurately integrate a weak signal since the two areas ignored which lie outside the two threshold become significant. The immobilized enzyme column containing both glutamate oxidase and glutaminase could be reused for at least 500 repeated analyses without significant loss of activity. In addition, the enzyme column was stable for several months when stored in 50 mM acetate, 100 mM NaCl pH 5.3 at 4° C.

Selected electroactive substances known to interfere in amperometric detection using platinum vs. silver/silver chloride poised at $+0.7$ V were injected into the sample stream to determine whether the addition of the resin would alleviate the interference. Without the ion exchanger in place, the injection of ascorbic acid or uric acid (1 mM) to the present biosensor resulted in a response which was somewhat similar to that of 1 mM glutamine. Another common electroactive interferent, acetaminophen (1 mM), resulted in a response 20% that of glutamine. However, with the resin in place, both the uric acid and acetaminophen signals were completely suppressed and the ascorbic acid was reduced by 97%. These findings are of significant importance since uric acid was reported to be produced as a waste product in certain insect cell culture systems. For instance, during the cultivation of *Bombyx mori* (silkworm), the level of uric acid produced from ammonia after 10 days was about 60 μM whereas the level of glutamine was 2 mM. Ascorbic acid is often added as an antioxidant when serum free media are used to cultivate mammalian cells. In some cases, the initial level of ascorbic acid added is almost as high as that of glutamine (0.3 mM). Without the anion exchanger in place, there would have been some error in the measurement of glutamine due to the presence of such interferents.

Figure 5:
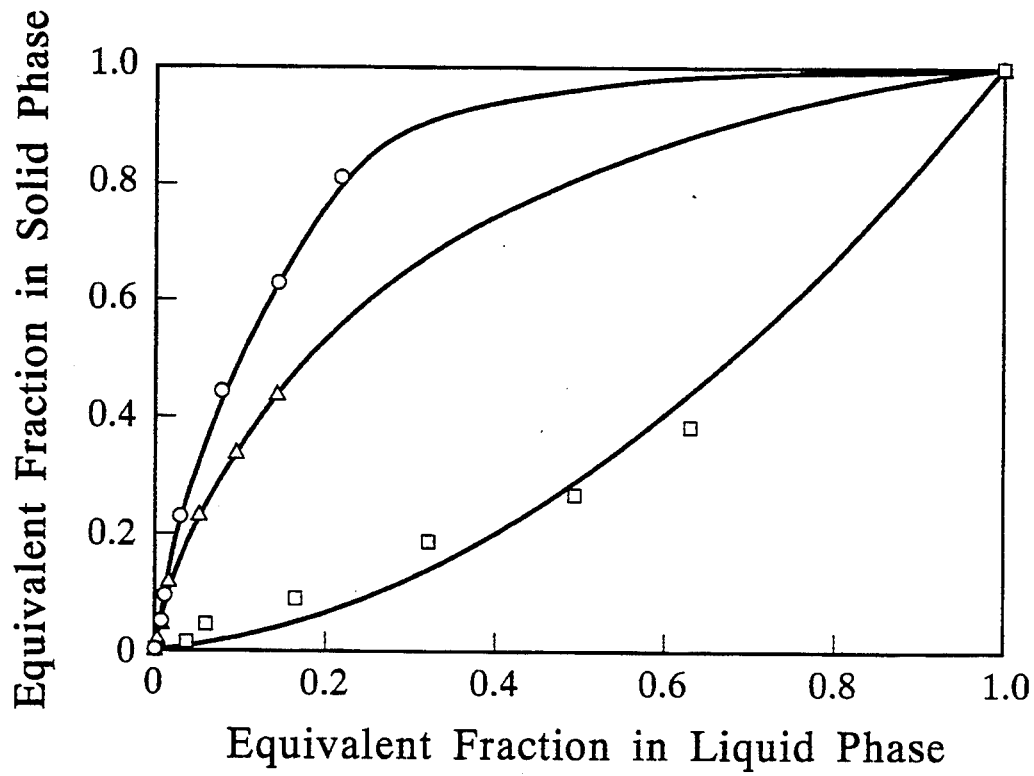
FIG. 5 illustrates ion exchange isotherms for ascorbic acid, uric acid and acetaminophen.

Ion exchange isotherms for the selected interfering compounds were also constructed in order to generate selectivity information for the various interfering compounds of interest. FIG. 5 illustrates ion exchange isotherms for ascorbic acid (○), uric acid (Δ), and acetaminophen (□) performed under the following conditions:

Ascorbic acid: equilibrate 0.5 g dry resin in 15 ml of a 0.1N solution containing both ascorbic acid and acetate anions at pH 4 and 21° C. The X and Y axes are defined as ascorbic acid/(ascorbic acid+acetate);

Acetaminophen: equilibrate 0.25 g dry resin in 15 ml of a 0.05N solution containing both acetaminophen and acetate anions at pH 4 and 21° C. The X and Y axes are defined as acetaminophen/(acetaminophen+acetate);

Uric acid: equilibrate 0.01 g dry resin in 15 ml of a 1 mM solution containing both uric acid and acetate anions at pH 6 and 21° C. The X and Y axes are defined as uric acid/(uric acid+acetate).

Figure 6:
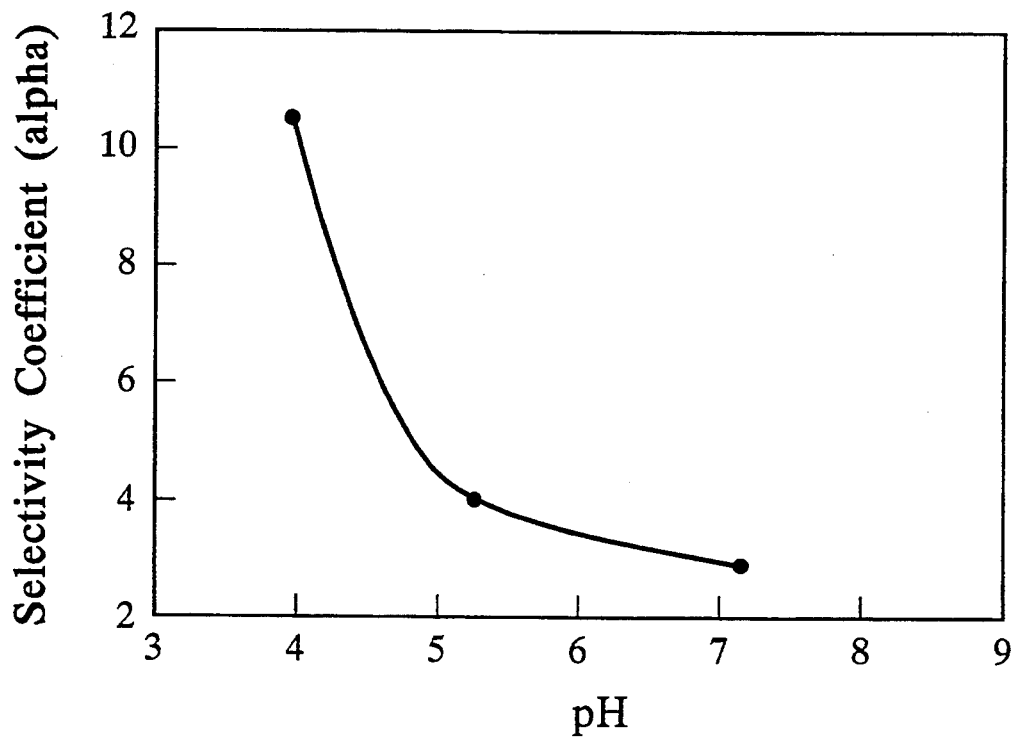
FIG. 6 shows the effect of pH on the selectivity coefficient of ascorbic acid.

As shown in FIG. 5, the resin has favorable isotherms which show high affinity for ascorbic acid and uric acid in competition with acetate anion. Such results were not completely unexpected since both uric acid and ascorbic acid are negatively charged at this operating condition and should bind to the anion exchange resin. The selectivity coefficient defined as $Y(1-X)/X(1-Y)$ was determined to be 10.5 for ascorbic acid and 7 for uric acid, respectively where X and Y are the equivalent fractions of ascorbic acid or uric acid in the solution and in the resin. The binding capacity of the ion exchanger for specific anions was also observed to be highly pH dependent. The selectivity coefficient for ascorbic acid decreased from 10.5 to 2.9 as the pH increased from 4 to 7.2 (FIG. 6).

Aspartic acid was also completely removed by the ion exchange column, i.e. the addition of the ion exchange column also improves the selectivity of the biosensor system of the invention for glutamine. Glutamate oxidase is known to oxidize aspartic acid in addition to glutamate so that the presence of the former acid at high level may cause some interference. The binding capacity of acetate anion resins to aspartate was anticipated since its structure is similar to that of glutamate, i.e. aspartic acid also possesses a carboxyl group on its side chain and has an isoelectric pH of 2.98.

Measurement of Glutamine in Cell Culture

Before testing real samples from insect and mammalian cell culture media, the system as illustrated in FIG. 1 and described hereinabove was run continuously with spent medium diluted ten-fold. In the case of mammalian cell culture this would result in a glutamate concentration of approximately 0.1 mM. With the 100–200 mesh resin, glutamate was first detected after 80 injections whereas with the 200–400 mesh, 200 injections could be performed, which corresponded well with the 2.5 times increased binding capacity of the 200–400 mesh observed previously (17 vs 7 mg). In the case of the insect cell culture medium, a ten-fold dilution results in a glutamate concentration of about 0.35 mM. Using the 200–400 mesh, 70 injections were possible before the glutamate began to be detected which results in a similar binding capacity as the mammalian culture. The amount of glutamate injected in both cases would have been about 0.35 mg. The lower capacity when compared to the pure glutamate samples is likely due to the other anions in the sample which will bind to the resin lowering the effective binding of glutamic acid. As well, the ionic strength of the sample will certainly be higher than that of the pure glutamate which would cause the bound glutamate to release more rapidly.

Figure 7:
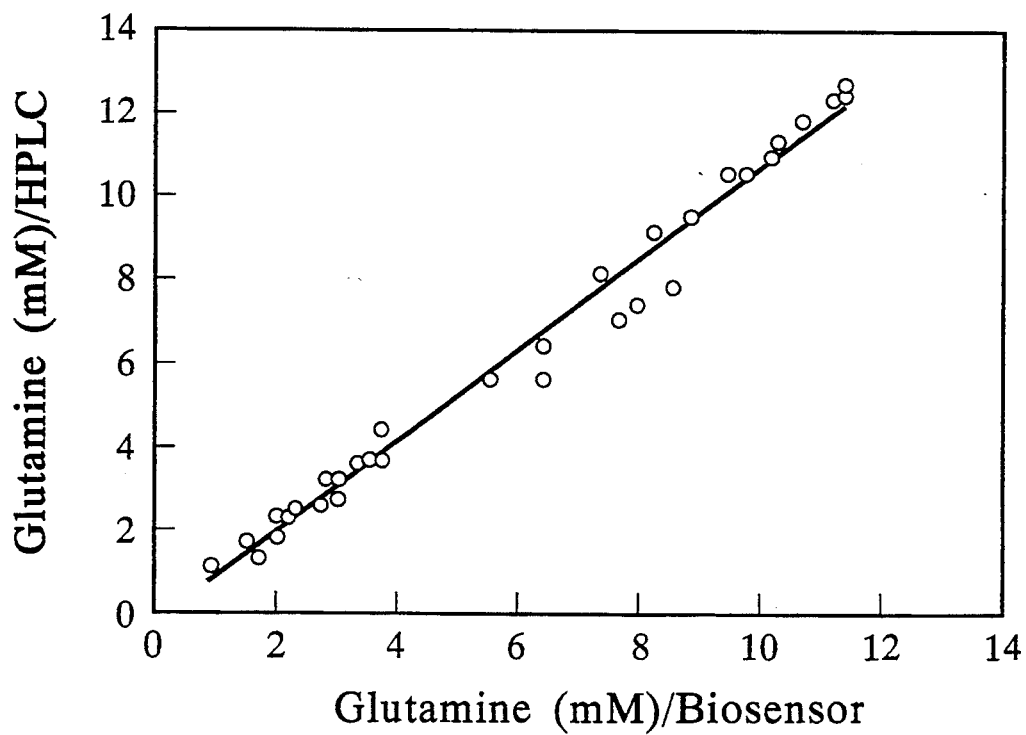
FIG. 7 is a graph comparing glutamine concentration results obtained by HPLC and the biosensor of the invention.
Figure 8:
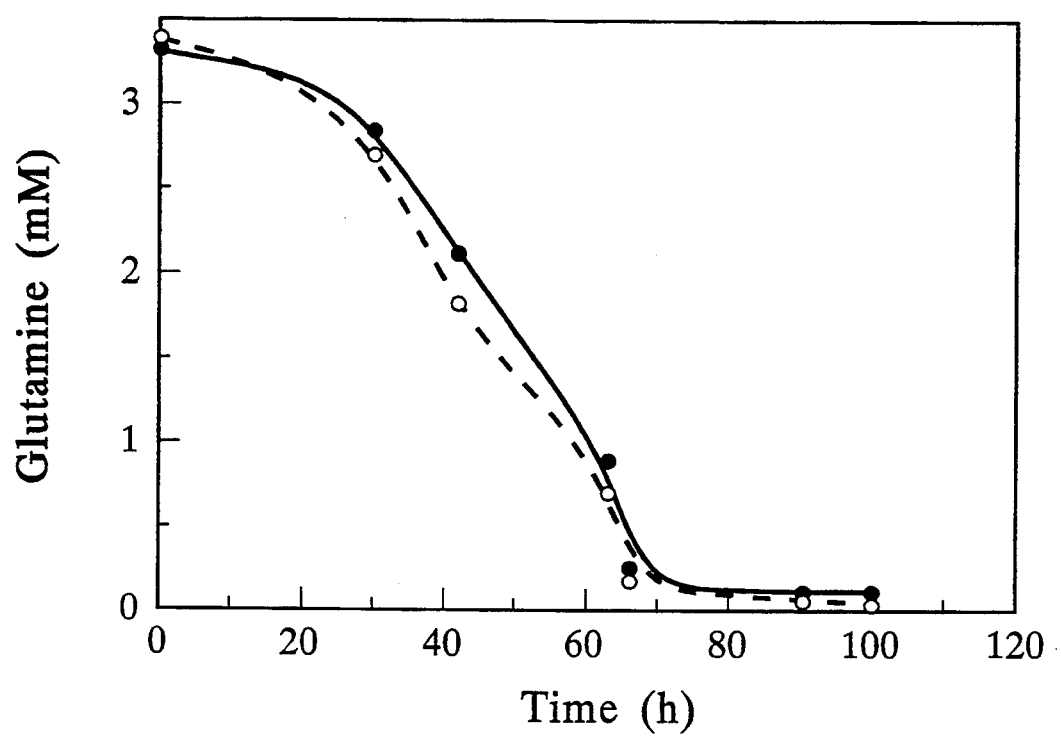
FIG. 8 is a graph of glutamine concentration profile vs time, obtained by HPLC and by the method and apparatus of the invention during the cultivation of a mammalian cell culture.
Figure 9:
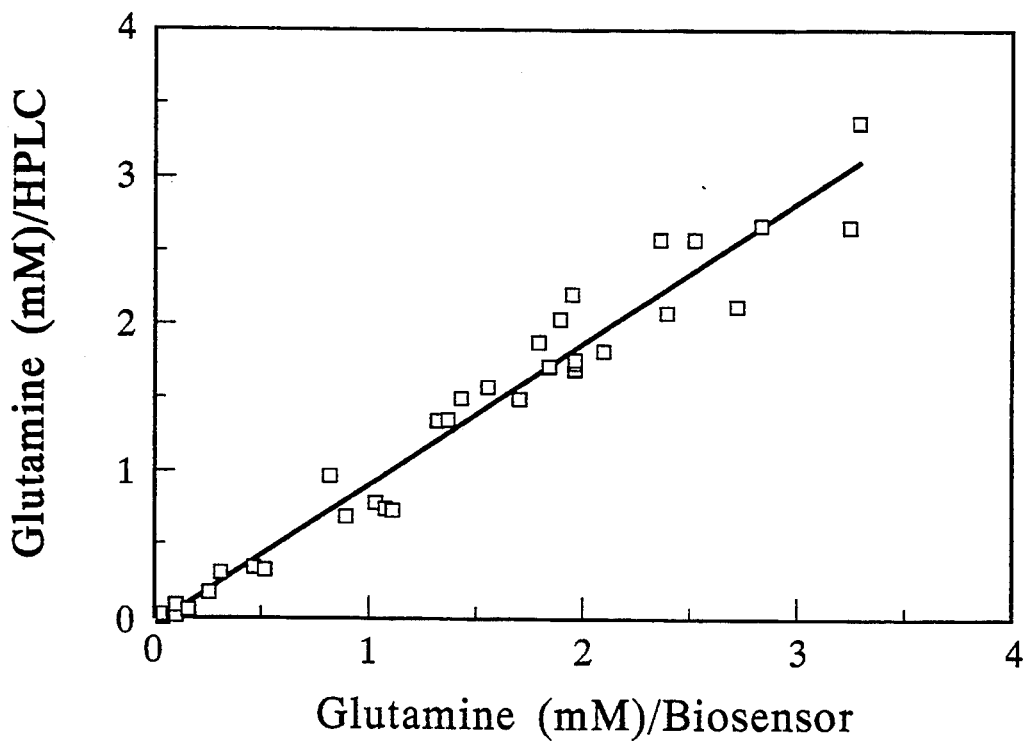
FIG. 9 is a graph comparing the glutamine concentration results for a mammalian cell culture, obtained by HPLC and by the apparatus and method of the invention.

The biosensor system of the invention equipped with the 200–400 mesh acetate resin column was then applied to determine glutamine in insect cell culture medium. The data obtained by the biosensor compared well with those of the HPLC method for a time course experiment. Alternatively, the biosensor values when plotted against those of HPLC resulted in a straight line with a slope of 1.056 and a correlation coefficient of 0.998 (n=32), as shown in FIG. 7. Similarly, good agreement was observed between the biosensor and HPLC for a time course experiment with a mammalian cell culture (FIG. 8; ● denotes HPLC and ○ denotes the biosensor of the invention). The biosensor values when plotted against those of the HPLC method resulted in a straight line with a slope of 0.937 and a correlation coefficient of 0.993 (n=39) as shown in FIG. 9.

Such good agreement thus validates the applicability of the biosensor of the invention for measuring glutamine levels in insect cell cultures as well as in mammalian cell cultures.

Glucose Determination

The apparatus described above can be adapted to monitor glucose by substituting glucose oxidase in the reactor 16 for glutaminase/glutamate oxidase.

Materials

β-D-glucose, glutaraldehyde (25% m/v), ATP, NADP, uricase (EC.1.7.3.3), glucose oxidase type X-S from *Aspergillus niger* (E.C. 1.1.3.4), hexokinase type VI, glucose 6-phosphate dehydrogenase type IX, catalase, and porous aminopropyl glass beads were purchased from Sigma (St. Louis, Mo.).

Immobilization of Glucose Oxidase on Aminopropyl Glass Beads

Two hundred and fifty mg of aminopropyl glass beads (80–120 mesh, 70 nm pore size) were washed extensively with phosphate-buffered saline, PBS (9 g/L sodium chloride, 20 mM phosphate, pH 7) and then activated by contacting with 3 mL of 2.5% (w/v) glutaraldehyde in PBS for 2–3 h at room temperature (20°–24° C.). The resulting orangish-pink beads were washed thoroughly with PBS followed by 20 mM phosphate, pH 7, to remove excess glutaraldehyde.

A 3 ml solution of glucose oxidase (547 U/mL and 205 U/mg solid) in 20 mM phosphate buffer, pH 7, was then covalently immobilized to the batch of activated beads and rotated end-over-end in a capped test tube overnight at 4° C. Experimental results confirmed that there was no evidence of any enzyme activity or protein content in the supernatant. After immobilization, the beads were packed into a piece of tygon tubing (2.54 mm ID, 6 cm in length), furnished with glasswool at the ends to retain the beads (0.25 g of beads will pack into approximately two columns). The enzyme column was stored in 50 mM acetate/500 mM NaCl buffer, pH 5,5, at 4° C. Optimum operating conditions for glucose conversion were determined with respect to buffer type and strength, pH, NaCl concentration, enzyme column length, and flow rate.

Anion Exchange Resin

The resin used and its preparation were virtually identical as for glutamine determination.

Determination of Glucose in Urine Samples

The anion exchange column was placed in the sample flow line upstream of the glucose oxidase column in order to remove endogenous uric acid from the samples. Urine samples were taken from healthy males (30–47 years old) and diluted five-fold by 1 mM acetate buffer, pH 5.5. Calibration of the FIA biosensor for β-D-glucose was performed by spiking a diluted urine sample with known concentrations of β-D-glucose (0.1, 0.2, 0.3 mM). A 157 mM β-D-glucose equilibrated for 2–3 hours will consist of 100 mM β-D-glucose and 57 mM α-D-glucose. The samples were analyzed for β-D-glucose by the system of the invention as well as the standard hexokinase assay. For the enzymatic assay, urine samples were further diluted two-fold in 150 mM phosphate buffer, pH 7.8, and measured in the presence of excess glucose 6-phosphate dehydrogenase, NADP, ATP, and $MgCl_2$. The metabolite assay was initiated by the addition of hexokinase, and the change in absorbance was monitored at 340 nM. It should be noted that the hexokinase assay measures the total D-glucose pool which contains 64% β-D-glucose and 36% α-D glucose form. Consequently, this must be taken into account in comparison with the results obtained by these two methods.

The uric acid content of the urine samples could be determined by monitoring the blank amperometric response of the urine sample in the absence of both the anion-exchange and immobilized enzyme columns. The sample was then reanalyzed after reaction with excess uricase and catalase, which removed the uric acid component of the interfering blank.

The glucose oxidase column was first used together with the FIA system without the anion exchange column in place to establish optimal operating conditions. At the preset flow rate of 31 ml/h, the response to 1 mM glucose increased with an increase in the column length up to 2 cm. Beyond this level, the response was no longer dependent on the column length. In view of the reusability of the immobilized glucose oxidase, a column length of 6 cm was chosen for all subsequent experiments. This series of experiments was performed in peak area to account for the difference in peak heights caused by changing dispersions owing to varying column lengths.

The optimal pH for soluble glucose oxidase was reported to be 5.6, however, after immobilization, glucose oxidase response to glucose was maximal over the pH range 4.5–7. Such behavior should be expected since a very large excess of glucose oxidase immobilized onto aminopropyl glass beads could easily overcome the pH dependency in the pH range tested. It should be important to note that at pH 5.5, uric acid exists mainly as negatively charged urate, which could be retained by the anion exchange resins. Therefore, a pH of 5.5 was chosen for all subsequent experiments. Among four different buffers tested at pH 5.5—acetate, citrate, imidazole, and phosphate—the response was somewhat similar, and acetate was selected in view of its buffering capacity over the desired pH range. Acetate buffer strength in the range 20–500 mM had no effect on the response to glucose, and 100 mM acetate was considered sufficient for maintaining the pH of the buffer in the column after mixing with the sample stream. Addition of sodium chloride to the buffer was necessary to prevent fouling of the immobilized enzyme column as well as the electrode surface. Concentrations of NaCl between 50 mM and 1.5M exhibited very little effect on the glucose response, and 1M NaCl was used for further experiments.

The response to 1 mM glucose remained constant as the sample flow rate increased over the range of 15–75 ml/h. Theoretical predictions for FIA systems expect a decrease in response as flow rates increase. However, in this case, the large excess of glucose oxidase immobilized on the beads likely overcomes this phenomenon in the range tested, and this characteristic may only be observed at even higher flow rates. A flow rate of 31 ml/h was selected for this study, and the total flow rate through the immobilized enzyme column will be 62 ml/h after the two streams merge.

Selection of the Type of Anion Resin for Removal of Uric Acid

The work was focused on the removal of endogenous uric acid from urine sample by anion exchange resins. Anion exchange resin AG 1-X8 (trademark) containing quaternary ammonium functional groups is capable of exchanging anions and possesses the following order of selectivity: Cl > acetate > OH. Columns containing the three above resin forms were monitored using the configuration shown in FIG. 1. The injection of uric acid to the system of the invention should provide minimal or no response since at pH 5.5, uric acid exists mainly as negatively charged urate (pI=5.4) and will be retained effectively by the anion exchanger. On the other hand, the response to glucose of the system should be similar with or without the ion exchange resin, since glucose is not ionized at this pH and passes through the ion exchange column.

To select the most suitable type of resin, a series of experiments was performed using a very large particle size resin, 20–50 mesh, in order that the effects would be more pronounced. Among the three different types tested (hydroxyl, chloride, acetate), the response to uric acid (1 mM) was 2.0, 0.40, and 0.25%, respectively, when compared with the signal obtained without the ion exchange in place. As a result, the acetate form of the resin was chosen for subsequent experiments to establish optimal operating conditions for the removal of uric acid.

The acetate buffer concentration used in the sample stream affects the binding capacity of the acetate resin (20–50 mesh) for uric acid. At low concentration of acetate (less than 5 mM) very little uric acid passed through (<1%), whereas at higher concentrations (100 mM), a larger amount of uric acid was detected (5%). Also as expected, the sample stream flow rate affected the uric acid binding capacity of the acetate resin column. At higher flow rates (>90 ml/h), 4% of the uric acid was observed to pass through the column. Obviously, there was a minimum residence time required for a complete interaction between uric acid and the anion exchanger.

Maximal Uric Acid Binding to the Acetate Resin Column

To be practical in the system of the invention, the resin must be effective for an extended period of time, so that adsorbed uric acid does not dissociate during the course of repeated measurements. The binding capacity of the two smaller particle sizes (higher binding surface areas) of acetate resins, 100–200 and 200–400 mesh, were evaluated by repeated injections of 5 mM uric acid (in 1 mM acetate). Uric acid began to pass through the column after 370 injections as detected by the biosensor with the 200–400 mesh resin and after only 200 injections with the 100–200 mesh. Based on this result, the maximum binding capacity of 200–400 and 100–200 mesh acetate resins was estimated to be 23.3 and 12.5 mg of uric acid, respectively. As expected, increasing the surface area for binding resulted in an increased uric acid binding efficiency, and as a consequence, the 200–400 acetate mesh was used for real samples.

Optimal Operating Conditions of the System with Acetate Resin

The binding capacity of the acetate resin (200–400 mesh) column as a function of the acetate buffer concentration used in the sample stream was reconfirmed. Under continuous injections of 1 mM uric acid at high acetate concentration (100 mM), the column was only good for 16 injections. However, as the acetate concentration was decreased, the efficiency of the column was improved. At 20 mM acetate, the column could be reused for 80 repeated injections before uric acid was detected. As a result, 1 mM acetate was chosen as the optimal running condition, since the column was observed to last for about 900 repeated injections of 1 mM uric acid.

Unlike the behavior of the 20–50 mesh resin, samples containing uric acid passed through the 200–400 mesh acetate resin at flow rates up to 90 ml/h without significant detection (<1%). By decreasing the particle size, the residence time is no longer critical, and the selected speed of 31 ml/h was considered compatible with the immobilized glucose oxidase column. The pH of the sample in the range of 5.5–5.7 did not have any noticeable effect on the binding efficiency of uric acid.

Response of the System to Glucose and Interference Studies

In peak height mode, there was an excellent linear response of the system of the invention to glucose up to 1 mM (correlation coefficient of 1). The sensitivity of the system was determined to be 160±2.4 RU/$\mu$m (95% confidence interval, n=10) with a minimum detection level of 10 $\mu$M. A good reproducibility (±0.23%) was obtained as reflected by the average response for 20 repeated analyses of 1 mM glucose (158,700±358 RU at 95% confidence interval). Each assay could be performed in 4 min, including washing giving a throughput of 15/h. Similarly, the response was also linear using peak area mode, however, the minimum detection level was considerably higher (50 $\mu$M). The immobilized enzyme column could be reused for at least 1000 repeated analyses without loss of activity and was stable for several months if stored at 4° C. in 50 mM acetate 500 mM NaCl, pH 5.5.

Without the anion exchanger, the system using immobilized glucose oxidase detects both uric acid and glucose (and also a number of other interfering substances, as ascorbic acid, or acetaminophen) in a similar manner with respect to sensitivity. The response to a mixture containing an equimolar ratio of glucose and uric acid was further found to be additive. Such a result thus leads to a conclusion that uric acid (and other interfering substances) must be removed from the sample, otherwise it will interfere with amperometric detection of glucose and produce a falsely elevated result. The introduction of the ion exchange (acetate) column to the system of the invention, completely blocks the uric-acid-interfering signal leaving just the detection of glucose. The peak height obtained for glucose (0.5 mM) was identical to that for a mixture of glucose and uric acid (0.5 mM each). The peak height for glucose was slightly lower (85%) because of dispersion effects when compared to the peak heights for glucose without the acetate resin.

Other electroactive substances known to interfere in amperometric detection were injected into the sample stream to determine whether the addition of the resin would alleviate the interference. Without the ion exchanger in place, the injection of ascorbic acid (1 mM) and acetaminophen (1 mM) resulted in responses of 100 and 20%, respectively, in comparison to glucose. However, with the resin in place, the acetaminophen signal was completely suppressed and the ascorbic acid was reduced by 90%. Both of these interferents may be present in urine, and therefore, their removal will further improve the selectivity of the system of the invention for detecting glucose.

Measurement of Background Signal in Urine Samples

The interference of electroactive uric acid in urine was first investigated, since the platinum electrode (poised at +0.7 V vs silver/silver chloride) should respond to urine owing to its high uric acid content (4–10 mM). In this experiment, the acetate anion-exchange column was removed from the biosensor system and a blank porous glass beads column substituted for the immobilized glucose oxidase column. As expected, the urine sample produced a very significant interfering signal. The response to uric acid was then confirmed by treating the urine sample with uricase and catalase to convert uric acid to noninterfering allantoin and water. In this case, the background signal was reduced by approx. 90%.

The measurement of urinary glucose was first attempted by replacing the blank column with the glucose oxidase enzyme column. The resulting signal, however, was only ca. 10% higher than the background signal. Such a result was somewhat anticipated, since the urine sample normally contains about 1 mM glucose or less. Therefore, the differential measurement was not considered satisfactory for the determination of urinary glucose in view of the signal-to-background ratio. Consequently, the removal of uric acid from urine is a prerequisite for reliable determination of glucose by amperometry.

With the anion exchange resin in place together with the blank column of glass beads, the background signal was reduced by more than 99%, an indication of strong binding between urate and the anion exchanger. When the blank column was replaced by the immobilized enzyme column for the measurement of the urinary glucose, the resulting signal-to-background ratio was always higher than 3, depending on the level of glucose in urine. Such data thus provided confidence for using the system of the invention comprising both the anion exchange and immobilized glucose oxidase columns for the determination of urinary glucose.

Measurement of Urinary Glucose

The biosensor system was first run continuously with a urine sample in the absence of the immobilized glucose oxidase column to determine the binding capacity of the anion-exchange column. Urine samples were diluted five-fold with a corresponding concentration of 0.6 mM for uric acid. Uric acid was first detected after about 65 injections, i.e. the column only retained up to 0.56 mg uric acid. The lower binding capacity of the column when compared to the pure uric acid samples is likely the result of other anions in the sample that will bind to the resin lowering the effective binding of uric acid. As well, the ionic strength of the sample will certainly be higher than the pure uric acid sample, which would cause the bound uric acid to release more rapidly. Since the level of uric acid in real samples varies from 4 to 10 mM, a conservative estimate for the reuse of the acetate column before replacement would be about 25-30 injections. The system of the invention equipped with the acetate resin column was then applied to determine glucose in the urine. The standard calibration for glucose was performed by spiking a urine sample with known concentrations of glucose and determining the peak heights by their differences compared to the urine sample alone. These peak heights were about 10-15% lower than those obtained using glucose alone. This phenomenon occurs because of widening of the peak base when using real samples.

Alternatively, peak area could be used, but owing to the lack of sensitivity and the low level of glucose in many urine samples, the above spiking protocol was preferred. The background signal was subtracted from the total signal by measuring the urine sample with a blank glass bead column rather than the glucose oxidase column.

The data obtained by the system of the invention compared well with those of the standard hexokinase enzyme assay. The biosensor values plotted against those of the enzyme assay resulted in a straight line with a slope of 0.99 and a relation coefficient of 0.97 (n=15). Such good agreement thus validated the applicability of the system of the invention for measuring glucose levels in urine.

To summarize, a system has been provided which can use immobilized enzymes such as glutamate oxidase and glutaminase in combination with a hydrogen peroxide electrode for the determination of glutamine in both insect cell and mammalian cell cultures. The system can also use immobilized glucose oxidase together with a hydrogen peroxide electrode for the direct determination of glucose in urine and blood samples. Consequently, the determination of either glutamine or glucose can be performed in a single step. In addition to glutamate (glutamic acid), aspartate and the three electronegative interferents: acetaminophen, ascorbic acid, and uric acid were also effectively adsorbed by the acetate ion exchanger. The introduction of this type of ion exchanger thus improves the selectivity of the biosensor system and extends its applicability to other biological fluids.

We claim:

1. A detection system for measuring glutamine in a liquid sample using enzymatic degradation of glutamine and amperometric detection of the resulting product or element, in the presence of compounds interfering with the measurement, the system comprising in combination:
    a) an ion exchange means capable of at least partly removing from the sample passed therethrough the interfering compounds while leaving the measured glutamine therein by virtue of a difference in their respective electric charges,
    b) immobilized enzymes glutaminase and glutamate oxidase for the enzymatic degradation of the measured glutamine, the enzymes being associated with the ion exchange means downstream thereof, and
    c) a sensor capable of sensing a product or element resulting from the enzymatic degradation of said glutamine to produce a signal indicative of the concentration of glutamine in the sample.

2. The system according to claim 1 wherein the ion exchange means is an anion exchange means.

3. The system according to claim 1 wherein the sensor is a hydrogen peroxide electrode.

4. A method of measuring glutamine in a liquid sample containing substances normally interfering with the measurement of said glutamine by enzymatic degradation of said glutamine and amperometric detection of a product or element resulting from the enzymatic degradation, said method comprising:
    a) passing the sample through an ion exchange means at a pH selected to impart a different electric charge on the particles of the interfering substances in said sample compared to the electric charge on the particles of the glutamine, to effect at least a partial retention of the interfering substances by said ion exchange means, then
    b) subjecting said sample to enzymatic degradation to form an enzymatic reaction product, and
    c) sensing the concentration of said reaction product or of another compound or element consumed or liberated in the formation of said product, said concentration being indicative of the concentation of glutamine in the sample.

5. The method according to claim 4 wherein the enzymatic degradation is carried out using glutamate oxidase and glutaminase, the interfering substances are one or more from the group consisting of glutamic acid, aspartic acid, uric acid and ascorbic acid, and the pH of the sample is lower than the isoelectric point of glutamine, but higher than the highest isoelectric point of the interfering substances present in the sample.

6. The method according to claim 4 wherein the ion exchange means is an anion exchanger.

7. The method according to claim 6 wherein the ion exchange means is an acetate anion exchange resin.

* * * * *